United States Patent
Varney et al.

[11] 3,971,255
[45] July 27, 1976

[54] EXERCISE APPARATUS

[76] Inventors: Justin Arnold Varney, 7326 Oglesby Ave., Los Angeles, Calif. 90045; Thomas Aquinas Feeney, 10108 Gaynor Ave., Sepulveda, Calif. 91343

[22] Filed: Aug. 4, 1975

[21] Appl. No.: 601,599

[52] U.S. Cl. .................................. 73/379; 272/116
[51] Int. Cl.² ........................................ G01L 5/02
[58] Field of Search ............... 73/379, 380; 188/67; 272/79 R, 80, 82

[56] References Cited
UNITED STATES PATENTS

| | | |
|---|---|---|
| 2,680,967 | 6/1954 | Newman ........................... 73/379 R |
| 3,811,672 | 5/1974 | Simmons ........................... 272/79 R |

*Primary Examiner*—Jerry W. Myracle
*Attorney, Agent, or Firm*—William H. Pavitt, Jr.

[57] ABSTRACT

An energy converting exercise device comprising a housing and a shaft extending therethrough for frictionally resisted axial movement of the shaft relative to the housing. The housing includes adjustable braking means to allow the user to vary the level of resistance to such relative axial movement, and operatively associated with the shaft are readout means to indicate to the user in units of applied force the instantaneous level of resistance effective as he moves the shaft axially relative to the housing.

14 Claims, 8 Drawing Figures

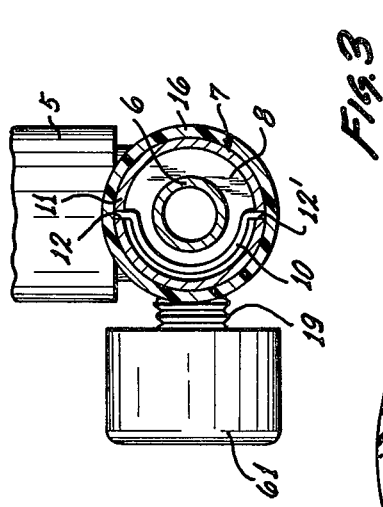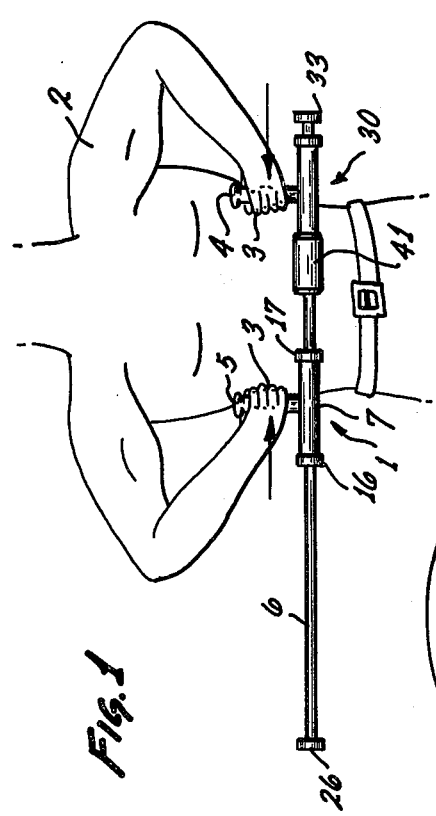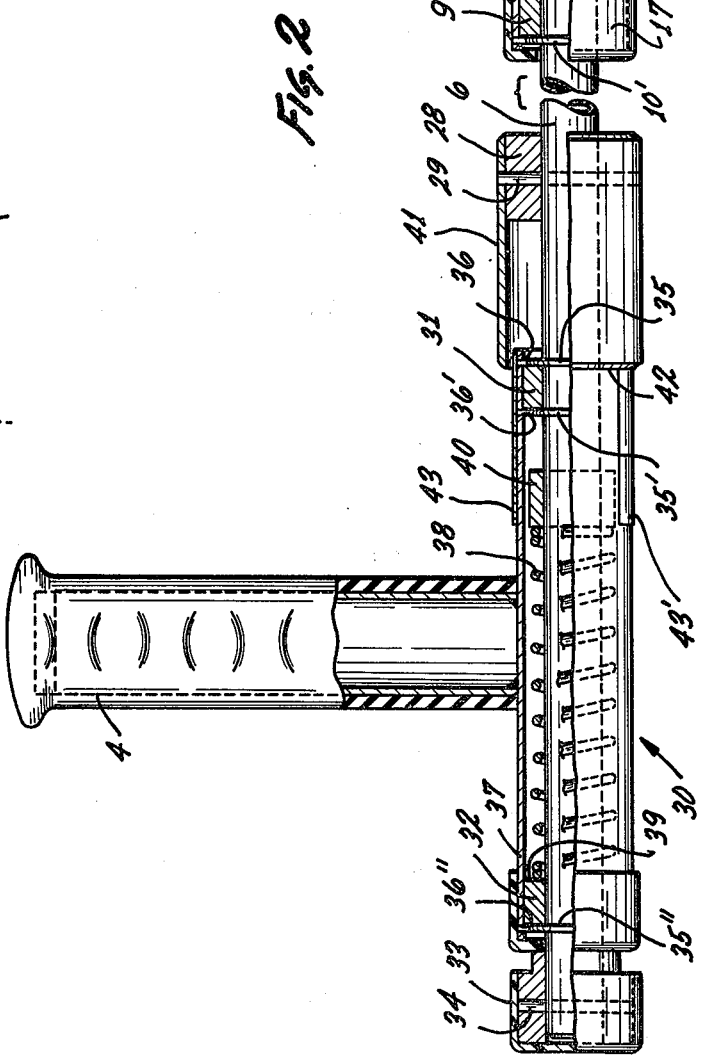

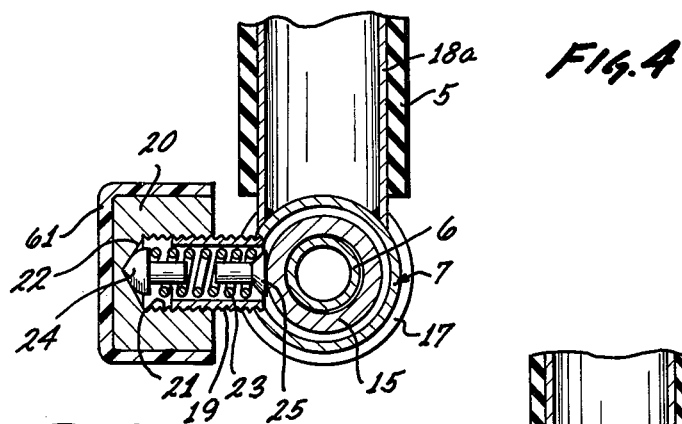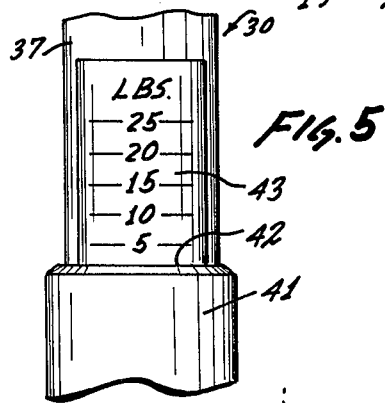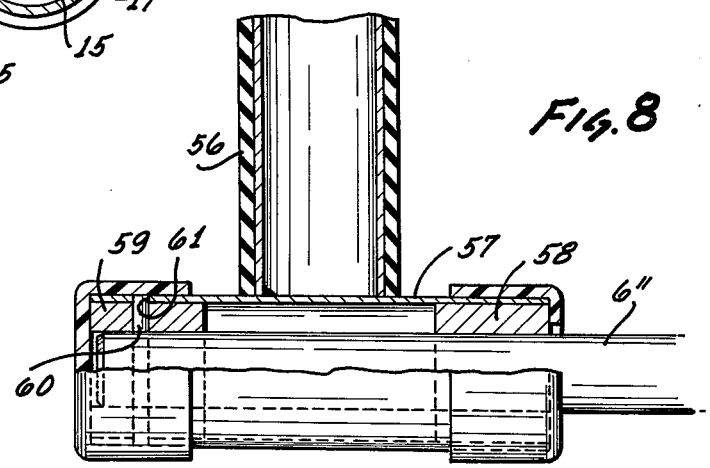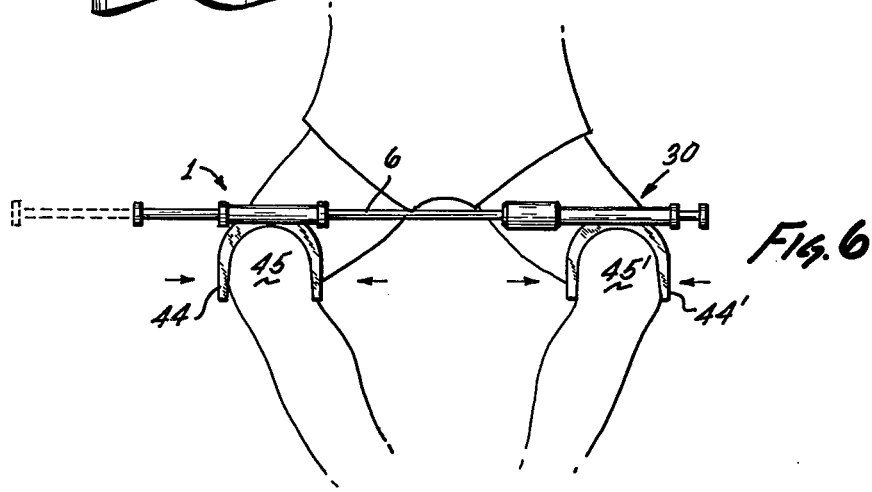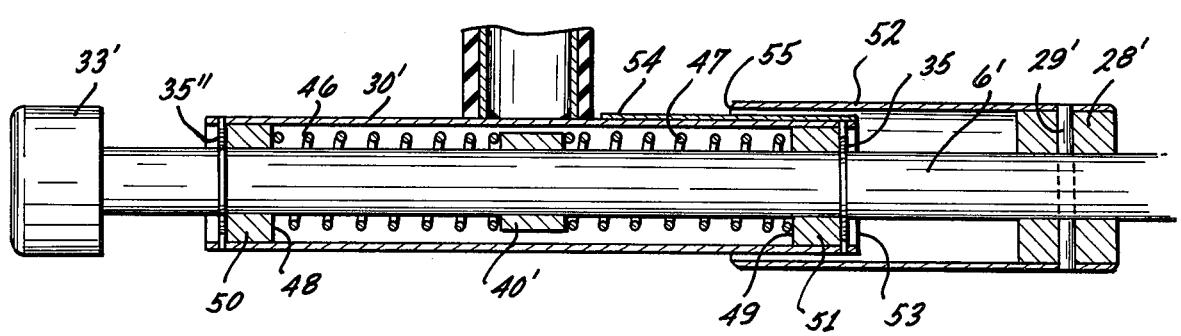

EXERCISE APPARATUS

BACKGROUND OF THE INVENTION

1. Field of the Invention

This invention relates broadly to the art of physical fitness exercisers and, more specifically, to the field of energy converting exercise mechanisms which provide means whereby the user can exercise selected muscle groups by overcoming resistance in repeated strokes or operational cycles of movement of one portion of the device relative to another portion.

2. Description of the Prior Art

Exercise devices of many types have been developed to allow the user to push or pull some portion of the device to the extent necessary to overcome resistance provided by the mechanism and thereby to allow the user to do work beneficial to particular muscles as an exercise for improving muscle tone and strength. One well-known category of such devices is characterized by the extension or compression of a yielding element such as a spring or rubber cord. A major disadvantage of such devices lies in the fact that the resistance provided is non-uniform, that is, the force required to overcome resistance through a working stroke varies from very little at the outset of deflection of the yielding member to some maximum level the user is able or willing to exert at an extended or compressed, as the case may be, state of deflection of the yielding member. Thus, the muscles involved do little or no effective work during the early portion of a stroke, on the one hand, and may be seriously over-stressed at the limit of deflection achieved by an over-zealous person. A further disadvantage of spring or elastic member exercise devices is the fact that resistance can usually be provided in but one sense of movement of one portion of the device relative to another, so that in any given exercise only those muscles overcoming that uni-directional resistance can be exercised. It is clearly more efficient and beneficial to exercise two synergistic sets of muscles in a given exercise routine as is possible with devices providing bi-directional resistance.

Another group of prior art exercise devices employs, for yielding resistance to be overcome by the user, various frictional means for converting the power output of the user into heat as he moves one portion of the device relative to another. Within this group are devices in which a flexible rope or cord is drawn by the user through a frictionally resistant tortuous path of movement among mechanical elements in a housing, or the rope or cord is squeezed by a braking device within a housing so that drawing the rope or cord through the housing is rendered difficult to a degree established by the user to the best of his ability. Among the disadvantages of this type of device is the great difficulty with which a desired level of resistance can be established by the user for any given exercise since the degree of frictional resistance to an applied force to draw the rope or cord through the device is heavily influenced by factors not controllable at all or controlled poorly at best by the user. A major and poorly controlled factor is the amount of back-tension in that portion of the rope or cord entering the resistance generating housing as the rope or cord is drawn through. Moderate back-tension can result in virtual immobilization of the unit thus defeating its purpose. Varying stiffness and thickness of the rope or cord can likewise produce highly variable resistance to the desired movement.

A further type of frictionally resistant mechanism which has been employed in exerciser devices involves a rigid shaft and a housing surrounding the shaft, such housing being fitted with braking means circumferentially engaging the shaft so that relative axial movement of shaft and housing may be variably resisted by the braking means. One such device incorporates in the housing a rope or cord wrapped around the shaft a number of turns. By varying the tension in this rope or cord, radial pressure of the rope or cord against the shaft is varied to provide a desired degree of frictional engagement of cord and shaft and thereby a desired level of resistance to movement of the shaft relative to the housing. Another device of this general type involves a number of circumferential rings of elastomeric material surrounding the shaft and enclosed in a housing. By compressing the stack of rings to varying degree in a confined zone by means of a threaded end cap on the housing, the rings are caused to grip the shaft through the medium of a sleeve-like member interposed between the shaft and the rings. Thus, a braking effect can be controlled to some extent. Both the aforementioned devices have the disadvantage of being highly sensitive to slight variations in diameter of the shaft along its working length. Thus, major variations in resistance to axial movement of the shaft relative to the circumferential braking means may be exhibited unless the shaft is a highly refined and consequently costly member.

Prior art devices discussed above exhibit a further common disadvantage, namely, that the user is provided no way of determining quantitatively what degree of resistance he is overcoming and therefore what force he is applying as he drives the moving element with respect to the fixed portion of the device. Accurate information on applied force is essential to performance of optimally designed exercise routines.

SUMMARY OF THE INVENTION

The present invention avoids and overcomes the problems encountered with prior art devices. In its preferred embodiment, the invention may comprise a relatively short, tubular, first housing, open at both ends, and a relatively long, circular cross-section shaft member extending axially therethrough. The housing is fitted closely at each end with low friction, wear resistant bushings to guide the shaft for free movement through the housing. The bushings may be restrained from moving axially out of the housing by suitable retaining rings or their equivalent. Positioned between the end bushings within the housing and surrounding the shaft is a further bushing-like element or collar of an outside diamter somewhat less than the inside diameter of the tubular housing. In the preferred embodiment of the invention, this collar may be spaced midway between and apart from the end bushings by means of tubular spacers which are of an inside diameter larger than the diameter of the shaft. The lengths of the spacers are such that the combined lengths of the end bushings and the collar, plus the spacers themselves, are slightly less than the distance between the bushing retaining rings. When assembled as indicated, the bushings, spacers and collar offer essentially no restraint to free movement of the shaft through the housing.

Unitary with the housing and extending from the side wall thereof approximately midway between the ends of the housing, in the preferred form of the invention, may be a short projecting boss or tubular element threaded to accept a cap or knob with mating threads to contain coaxially therewith a plunger. The projecting member is positioned to coincide with a port in the wall of the housing so that the plunger positioned within the projecting member may extend through the wall of the housing to bear against the collar on the shaft. The plunger is of such length that it is contained with no clearance between the collar and the threaded cap or knob. Thus, by turning the cap or knob on its threads, the plunger may be forced with more or less pressure against the collar and the collar thereby controllably pressed against the shaft. Since the shaft is centrally supported in the housing by the two end bushings, a state of variable frictional engagement of the shaft between the two end bushings and the centrally disposed collar is realized, the degree of such frictional engagement being a direct function of the pressure exerted by the plunger against the collar. By selecting materials for the end bushings and collar of suitable coefficient of friction in sliding contact with the shaft, it has been found possible in practice to realize a highly desirable range of resistance to axial movement of the shaft through the housing as a function of pressure exerted by the plunger against the collar and, therefore, pressure of the collar against the shaft. Thus, manually adjusted means for effecting quick changes of resistance level are realized.

In order for adjustments to be conveniently sensitive, that is, for considerable rotation of the adjusting knob or cap to be required for marked changes in levels of resistance to relative axial movement of shaft and housing, the plunger placed in compression by the cap or knob may be a spring of suitable stiffness. Thus, as the cap or knob advances on its threads with rotation, the spring plunger deflects and exerts a corresponding axial force against the collar. Considerably more rotation of the adjusting knob or cap to produce a given change of pressure against the collar is thereby required than would be the case with a non-resilient plunger. The net effect is that highly sensitive adjustments in frictional resistance can be readily accomplished.

In the preferred form of the invention, the housing is fitted with means projecting from the side of the housing by which the user can apply force conveniently for driving the housing along the shaft. Such means may be a hand grip of conventional configuration or, for special exercise applications, a suitable bracket or yoke or the like for engagement with some portion of the user's body, such as the foot or knee. By placing the point of application of the driving force eccentric from the housing and shaft, the shaft may be of any length suited to the exercise purposes without interference between the shaft and that portion of the user's body applying the driving force.

Placing the point of application of the driving force eccentric from the shaft imposes the requirement that the shaft supporting bushings within the housing be spaced apart sufficiently to prevent jamming of the housing on the shaft due to cocking. The critical minimum space between bushings is a function not only of the extent of eccentricity of the point of application of the driving force from the shaft centerline but also of the effective coefficient of friction between the bushings and shaft. It is likewise important that the direction of the force applied by the plunger against the collar to produce a braking action be substantially normal to the plane defined by the centerline of the shaft and the point of application of the force tending to drive the housing along the shaft. The reason for this critical relationship lies in the fact that if the line along which the force applied to the collar is in the plane defined above, as opposed to substantially normal to that plane, it is possible at certain settings of the adjusting cap or knob, and therefore certain levels of force applied by the plunger against the collar, for the collar and only one end bushing to assume full support of the shaft, the other end bushing carrying substantially no load and providing little or no stabilizing effect. Under these conditions, the acting points of support of the shaft may be well under the critical spacing and a grabbing, irregular movement of the housing along the shaft results. Placing the axis of the plunger substantially at right angles to the plane defined by the shaft centerline and the point of application of the driving force overcomes this problem and yields smooth, stable action at all settings of the brake adjusting knob or cap.

In all frictionally resistant exercisers the instantaneous level of resistance to relative movement of the frictionally engaged elements is to a significant extent a function of the rate of such relative movement. This rate in turn is influenced heavily by the amount of force applied by the user to cause such movement. It is therefore intrinsically impossible in this type of device to pre-set a frictional resistance level with certainty that any given adjustment will relate directly to a desired level of applied force at a desired rate of relative movement. The practical solution to this apparent dilemma lies in the combination of an applied force measuring and indicating means with one or the other of the relatively moving elements so that the user can observe the actual instantaneous applied force he is generating during movement of the device. With such information available, he can readjust the braking means to yield the required effective resistance for a desired combination of applied force and rate of relative mevement.

The present invention incorporates in operative relationship to the shaft such applied force measuring and indicating means. A stop collar is fixed to the shaft. A second tubular housing with anti-friction bearings or bushings at each end is mounted on the shaft so that this second housing can move freely with respect to the shaft both axially and rotationally about the axis of the shaft. Between one end bearing, which is secured to this second housing so as to prevent axial movement relative thereto, and the stop collar, is a compression spring. In the preferred form of the invention, both the stop collar and the spring are inside the second tubular housing. The spring is of sufficient stiffness to avoid deflection to its solid height at the maximum force contemplated to drive the shaft through the housing containing the adjustable resistance means. Arranged in telescoping relationship with and outside the second housing is a cylindrical sleeve mounted fixedly on the shaft, one end of such sleeve thus serving as a reference for determining the position of the second housing as it moves telescopically within the sleeve. By positioning on the outer surface of the second housing a suitable scale graduated, for instance, in pounds, it is possible to read directly the force required to compress the spring and thereby move the second housing with respect to the sleeve to a position representing the applied force. By providing hand grip or other convenient force applying means on this second and force-readout housing, similar in function to such means on the first, frictionally resistant, sliding housing, it is convenient for the user to apply equal and opposite forces to move the two housings toward or apart from each other. As the first sliding, frictionally resistant housing is driven along the shaft, or, as a corollary, the shaft is driven through the first frictionally resistant housing, the user is able readily to observe the actual, instantaneous force he is exerting to produce the relative movement. It should be noted that the applied force readout means described above provides for force measurement in only one direction of movement of the shaft relative to the frictionally resistant housing. Since the effective resistance is the same in both directions of movement, it is usually sufficient to measure the force in but one direction. However, it is readily possible, if so desired, to provide force readout in both directions of movement as hereinafter illustrated and described in detail.

BRIEF DESCRIPTION OF THE DRAWINGS

In the accompanying drawings:

FIG. 1 is a front view of a person employing the exerciser by means of handgrips thereon;

FIG. 2 is an elevation partly in section of an embodiment of the invention equipped with hand grip means;

FIG. 3 is a sectional view taken on the line 3—3 of FIG. 2;

FIG. 4 is a sectional view taken on line 4—4 of FIG. 2;

FIG. 5 is a detail of an applied-force readout scale;

FIG. 6 is a front view of a person using an embodiment of the exerciser device fitted with yokes to engage the knees of the user;

FIG. 7 is a partial sectional view of a further different embodiment of the invention; and FIG. 8 is a side elevation partly in section of a modification of the embodiment illustrated in FIGS. 1–4.

DESCRIPTION OF THE PREFERRED EMBODIMENTS

FIG. 1, an embodiment of the exercise device 1 is shown as held typically by a user 2 by his hands 3 gripping hand grips 4 and 5. As shown in FIGS. 2 through 5, the exerciser device 1 comprises a shaft 6 of circular cross-section which may be solid or tubular metal of suitable physical properties. Adapted to slide axially along shaft 6 is a first housing 7 preferably of tubular cross-section to accept, in close-fitting diametral relationship, anti-friction bushings 8 and 9. In order to retain bushings 8 and 9 within housing 7, spring clips 10 and 10' are provided to engage wall 11 of housing 7 by means of holes 12 and 12' drilled through wall 11. Preventing bushings 8 and 9 from moving axially toward each other in housing 7 are spacer tubes 13 and 14 which abut collar 15 surrounding shaft 6. Collar 15, spacer tubes 13 and 14 and bushings 8 and 9 are all of an inside diameter to allow shaft 6 to slide freely therethrough. Collar 15 is of an outside diameter markedly less than the inside diameter of housing 7 so that even though collar 15 may be pressed from the side into tight engagement with shaft 6, and therefore out of axial alignment with bushings 8 and 9, the outer surface of collar 15 will not make contact with the inside surface of wall 11 of housing 7. Caps 16 and 17, each typically with an aperture 18 through which shaft 6 may move without restraint, are provided to enclose the ends of housing 7.

In the embodiment of the invention shown in FIGS. 1 and 2, hand grip 5, preferably of elastomeric material to facilitate gripping, is mounted on a laterally depended tubular projection 18a which may be unitary with housing 7 approximately midway between the ends thereof. Thus, a force applied to hand grip 5 substantially parallel to the axis of shaft 6 will tend to move housing 7 along shaft 6 if shaft 6 is restrained.

Referring to FIG. 4, it will be seen that adjacent projection 18a and extending from housing 7 substantially at right angles to both the axis of housing 7 and the centerline of projection 18a, is a tubular projection 19, the outer surface of which is threaded to engage mating threads in borehole 21 of knob 20. Borehole 21 extends to end wall 22 of knob 20. Interposed between end wall 22 of knob 20 and collar 15 is a spring plunger 23 which exerts a degree of force against collar 15 as a function of the axial position of knob 20 on projection 19. To facilitate grasping of knob 20 for rotation thereof, knob 20 may be fitted with a cap 61 of material and surface texture suited to the purpose. To further facilitate rotation of knob 20 as spring plunger 23 is compressed, plunger 23 may be fitted with an end bearing member 24 which presents a smooth, relatively friction-free surface for rotation relative to the inner surface of wall 22. The other end of plunger 23 may be fitted with a flat headed pin 25 to distribute the pressure imposed on collar 15 by plunger 23.

Traverse of housing 7 along shaft 6 is limited at one extreme by stop collar 26 which is secured to the end portion of shaft 6 by dowel pin 27. At the other limit of travel of housing 7, stop collar 28 is secured to shaft 6 by dowel pin 29.

In the preferred form of the invention, shaft 6 extends through and beyond stop collar 28 to provide for the mounting of applied force measuring and indicating means. Such means comprise a second housing 30, preferably tubular, fitted closely at each end with anti-friction bushings or bearings 31 and 32 to allow free axial and rotational movement of housing 30 relative to shaft 6. Limiting such free axial movement of housing 30 toward the adjacent end of shaft 6 is stop collar 33 which is secured to shaft 6 by dowel pin 34. Bushings 31 and 32 are secured within housing 30 by spring clips 35, 35' and 35" which may be identical in form to similarly employed clips 10 and 10' in housing 7 and which engage, respectively, holes 36, 36' and 36" in the wall 37 of housing 30. Not shown are corresponding holes in the opposite side wall of housing 30 which accept the respective opposite ends of clips 36, 36' and 36".

Coaxial with shaft 6 and inside housing 30 is compression spring 38 which abuts at one end the inner face 39 of bushing 32 and at its other end abuts stop collar 40. Stop collar 40 is fixed immovably on shaft 6 within housing 30 at an axial location relative to bushing face 39 such that spring 38 rests without substantial deformation from its free length when housing 30 is in abutment with stop collar 33.

In close-fitting relationship to stop collar 28 and affixed thereto by dowel pin 29 is tubular shell 41 extending in telescoping relationship over housing 30 to permit housing 30 to move freely into shell 41 as spring 38 deflects under load. Scales 43 and 43' are affixed to housing 30 and are graduated in suitable units of force such as pounds or kilograms as best seen in FIG. 5. The two scales 43 and 43' may be applied on opposite sides of housing 30 so that force measurements may be easily read with housing 30 in a variety of positions relative to the user's eyes.

Attached to, or integral with, housing 30 may be means to facilitate applying a force to housing 30 parallel to shaft 6. For purposes of illustration, hand grip 4, similar in function to hand grip 5 on housing 7, is shown as an example of such means. Other suitable fittings to allow convenient exercise of muscles in portions of the body other than the arms may be employed. FIG. 6 depicts, for instance, the exerciser fitted with rigid yokes 44 and 44' adapted to engage the knees 45 and 45', respectively, of the user.

Referring again to FIG. 2, it will be noted that means are shown for indicating applied force in one axial direction only relative to shaft 6, that is, in a direction toward housing 7 but not in the opposite direction. FIG. 7 illustrates in partial section that portion of the exercise apparatus employed for providing applied force readout but in a configuration or embodiment capable of indicating a force level in either axial direction relative to shaft 6. Stop collar 28', as shown in FIG. 7, is positioned relative to stop collar 33' to allow a certain amount of movement of housing 30' as shown. Such at-rest position is determined by identical compression springs 46 and 47 which abut stop collar 40' affixed immoveably on shaft 6' within housing 30'. Springs 46 and 47, respectively, abut inner faces 48 and 49 of bushings 50 and 51 respectively. Bushings 50 and 51 are retained in housing 30' by suitable spring clips such as clips 35, 35' and 35'' shown in FIG. 2.

Cylindrical shell 52, mounted in tight-fitting relationship on stop collar 28' and affixed thereto by dowel pin 29', extends in a telescoping relationship over housing 30' sufficiently far to allow housing 30' to move from its at-rest position, as shown, to a limit position determined by stop collar 33' without the end 53 of housing 30' emerging from within shell 52. A scale 54 is positioned on housing 30' so that a "O" mark is in the same plane as end 55 of shell 52 with housing 30' in the at-rest position. Graduations extending in both directions from the "O" line are located on the scale so as to indicate the number of pounds, for instance, of force causing at any given moment a displacement of housing 30' from its at-rest position, whether such displacement be in one axial direction or the other with respect to shaft 6'.

In some exercise situations it may not be important to be able to read directly the amount of force applied by the user as he performs his exercise routine. For such cases, the exercise may comprise only an adjustable resistance housing, such as a housing 7, to slide along a shaft such as shaft 6, and a hand grip or similar force applying means attached fixedly to one end of the shaft as depicted in FIG. 8. Such a fixed hand grip 56 may be unitary with a short tubular body 57 in which housings 58 and 59 are pressed to fit snugly on shaft 6''. To secure the assembly on shaft 6'', dowel pin 60 may be inserted in close fitting hole 61 drilled substantially on a diametral line through tubular body 57, bushing 59 and shaft 6''.

In operation, it may be seen that the device allows the user to exercise selected muscle groups by employing those muscles to drive housing 7 cyclically forth and back along shaft 6 by means of appropriate force-applying fixtures such as hand grips 4 and 5 or knee yokes 44 and 44'. The force applied to housing 7 is carried through shaft 6 and reacted to by an equal and opposite force applied to housing 30, or in the other embodiments illustrated and described, to housing 30' or to tubular body 57 which may be equipped with means to facilitate such application of force similar to those equivalent means associated with housing 7. In the case of that embodiment of the invention used to exercise the arms, the user may grip the two hand grips as depicted in FIG. 1, for instance, and alternately force the grips toward and apart from each other. When such applied force exceeds the level of resistance to relative axial movement established by a given setting of the resistance adjustments means, housing 7 moves along shaft 6 until either the force is removed or the housing arrives at a limit of travel determined by one of the stop collar 26 and 28. During such movement, the user may observe by means of scale 43 or 43' or by means of scale 54 in the bi-directional readout form of the invention, the actual, instantaneous level of force he is applying to cause the relative movement of housing 7 and shaft 6. If the force he applies to produce a given rate of movement is less or more than desired for the particular exercise in progress, the user can readily adjust the level of resistance by means of knob 20 on housing 7.

Rotation of knob 20 with respect to threaded projection 19 causes knob 20 to advance toward, or retreat from, collar 15 on shaft 6. As knob 20 advances toward collar 15, spring plunger 23 is compressed progressively to create a force directed against collar 15 and transmitted through the wall of collar 15 to shaft 6. Shaft 6 is thereby pressed against the respective walls of bushings 8 and 9, as shown in FIG. 2, which in turn transfer their respective shares of the thrust load of plunger 23 into the wall 11 of housing 7. Wall 11 of housing 7 transfers the load to projection 19 and hence, through the threaded engagement of projection 19 and knob 20, to wall 22 of knob 20. As will be readily understood by reference to FIG. 4, the degree of deflection of spring plunger 23 determines the amount of pressure exerted by plunger 23 against collar 15 and therefore by collar 15 against shaft 6 and, in turn, by shaft 6 against bushings 8 and 9. The effective coefficient of friction between shaft 6 and the inner surfaces of bushings 8 and 9 and collar 15 determines, for any given compressive load in spring plunger 23, the degree of frictional resistance to relative axial movement of shaft 6 and housing 7. Change of such resistance at the discretion of the user is therefore readily accomplished by appropriate rotation of the adjusting knob 20.

Operation of the applied force readout device may be described as follows: Upon application of a force to second housing 30 in the direction of first housing 7 and resisted by an equal and opposite force applied to first housing 7, second housing 30 moves to a limited extent along shaft 6 in the direction of first housing 7. Such movement is limited by the reaction of spring 38 interposed between stop collar 40 and anti-friction bearing 32. The greater the force applied to second housing 30, the greater the deflection of spring 38 until its reaction equals the applied force. Thus, second housing 30 moves to a point of balanced forces. As previously described, second housing 30 moves, as spring 38 deflects, in telescoping relationship into shell 41. Thus, the edge 42 of shell 41 serves as a convenient reference for determining the extent of such displacement of second housing 30 at the point of balanced forces. Scales 43 and 43' allow the user to observe directly the actual force he is applying as he urges first housing 7 toward second housing 30.

Applied force measurement in both directions of movement of first housing 7 along shaft 6 may be provided by the readout device shown in FIG. 7 and described heretofore. Operation of this form of readout device is essentially similar to that described above for the single-direction readout means except that housing 30' moves in a telescoping relationship to shell 52 in either direction from the neutral or at-rest position shown in FIG. 7. Scale 43, mounted on housing 30' is positioned so that its "0" reference line coincides with the edge 55 of shell 52 when housing 30' is in the at-rest or neutral position. Thus, the extent of movement of housing 30' from this neutral position incident to an applied force in either direction can be observed readily and interpreted directly in terms of the amount of such applied force causing deflection of either spring 46 or spring 47, as the case may be.

Operation of the exerciser in its use for exercising muscles other than those in the arms and shoulders is exemplified in FIG. 6 wherein the unit is shown fitted with yokes 44 and 44' adapted to embrace the knees 45 and 45', respectively, of the user. In this case, the user forces his knees toward and apart from each other cyclically so as to drive housing 7 along shaft 6 against a preset resistance, thus exercising the abductor and adductor muscles of the upper leg. Specialized attachment fittings similar to yokes 44 and 44' can be devised readily to adapt to other portions of the body, such as the ankles or feet.

It will be appreciated from the foregoing that the deficiencies and disadvantages of the prior art devices are completely overcome and avoided in the present invention. A nearly constant level of applied force throughout a stroke in either direction of movement is provided so that the muscles involved in a given exercise are worked beneficially throughout each stroke in each direction. Synergistic or opposing sets of muscles are worked in each exercise routine. The exact level of force applied for any given resistance setting can be observed by the user during his exercise. The braking means wherein a load for generating frictional resistance to relative axial movement of a housing and a shaft is applied normal to the shaft from one side at or near a midpoint between supporting bushings which are spaced considerably apart, and wherein the load applied for generating frictional resistance is itself exerted through resilient means, allows for variation in diameter of the shaft along its length without significant variation in resistance level as the shaft passes through the housing. Furthermore, means are provided both to allow highly sensitive adjustments of resistance to suit precisely the requirements of particular exercises and to allow the user to read directly the exact force he is applying during an exercise stroke. Thus, far greater precision of design and execution of exercises for particular purposes is rendered feasible and practical by the present invention in relation to the prior art devices.

We claim:
1. An exerciser device comprising
an elongate cylindrical housing;
a shaft slidably mounted in said housing and extending therethrough, said shaft and said housing being substantially coaxial;
bushing means adjacent each of the ends of said housing to support said shaft in spaced relationship to the wall of said housing; and
adjustable means in operative relationship to said housing for selctively applying a force against said shaft in a direction substantially normal to the axis thereof, whereby the degree of frictional resistance to movement of said shaft relative to said housing may be varied.

2. The device of claim 1 wherein said adjustable means includes a collar on said shaft adapted to accept said force for transfer to said shaft.

3. The device of claim 1 wherein said adjustable means includes rotatable means threadedly engaging the wall of said housing.

4. The device of claim 3 in which yielding means are interposed between said rotatable means and said shaft.

5. The device of claim 1 wherein said housing includes means depended therefrom and adapted to accept a driving force at an effective point of application eccentric from said shaft, said driving force tending to move said housing relative to said shaft.

6. The device of claim 5 in which the plane defined by the axis of said shaft and the effective point of application of said driving force is substantially normal to the direction of the force applied to said shaft by said adjustable means.

7. The device of claim 1 wherein said shaft includes means depended therefrom adapted to accept a force tending to move said shaft relative to said housing.

8. The device of claim 1 wherein said housing and said shaft include means depended therefrom and adapted respectively to accept equal and opposite forces whereby said housing and said shaft may be moved relative to each other by the application of such equal and opposite forces.

9. The device of claim 8 in which said depended means are hand grips.

10. The device of claim 8 in which said depended means are yokes adapted to engage the limbs of a person employing the exerciser.

11. An exerciser device comprising
a shaft;
a housing slidably mounted on said shaft, said housing including means for selectively varying the degree of frictional engagement between said shaft and said housing; and
applied force indicating means operatively associated with said shaft whereby the level of a force tending to cause axial movement of said shaft relative to said housing may be observed.

12. The device of claim 11 in which said force indicating means includes
an elongate housing mounted on said shaft and adapted for free axial movement relative thereto;
a stop collar fixedly attached to said shaft; and
yielding means disposed between said stop collar and said elongate housing whereby axial displacement of said shaft is resisted by said yielding means to a degree substantially commensurate with the level of a force applied to said elongate housing tending to move said elongate housing axially relative to said shaft.

13. The device of claim 11 in which said applied force indicating means includes
abutment means unitary with said shaft;
a tubular housing slidably mounted on said shaft;
yielding means interposed between said abutment means and said tubular housing;
a collar fixedly attached to said shaft in telescoping relationship to said tubular housing; and
at least one scale on said tubular housing arranged and graduated so as to register by reference to a point on said collar the amount of force causing said yielding means to deflect to a given extent.

14. The device of claim 11 in which said housing includes means depended therefrom for application of a force substantially parallel to the axis of said shaft; and in which said applied force indicating means includes means depended therefrom for application of a force substantially equal and opposite to said force applied to said housing.

* * * * *